United States Patent [19]

Minami

[11] Patent Number: 5,365,268
[45] Date of Patent: Nov. 15, 1994

[54] CIRCUIT BOARD OF SOLID-STATE IMAGE SENSOR FOR ELECTRONIC ENDOSCOPE

[75] Inventor: Itsuji Minami, Omiya, Japan

[73] Assignee: Fuji Photo Optical Co., Ltd., Omiya, Japan

[21] Appl. No.: 82,913

[22] Filed: Jun. 29, 1993

Related U.S. Application Data

[63] Continuation of Ser. No. 866,575, Apr. 10, 1992.

[30] Foreign Application Priority Data

Apr. 26, 1991 [JP] Japan .................................. 3-125327

[51] Int. Cl.$^5$ ............................................... A61B 1/06
[52] U.S. Cl. ................................................... 348/76
[58] Field of Search ............... 358/98, 213.11; 128/6; 348/75, 76, 65

[56] References Cited

U.S. PATENT DOCUMENTS

| | | | |
|---|---|---|---|
| 4,745,470 | 5/1988 | Yabe | 358/98 |
| 4,809,680 | 3/1989 | Yabe | 358/98 |
| 4,832,003 | 5/1989 | Yabe | 358/98 |
| 4,890,159 | 12/1989 | Ogiu | 358/98 |
| 5,021,888 | 6/1991 | Kondou | 358/213.11 |
| 5,040,069 | 8/1991 | Matsumoto | 358/98 |

Primary Examiner—Tommy P. Chin
Assistant Examiner—Bryan S. Tung
Attorney, Agent, or Firm—Ronald R. Snider

[57] ABSTRACT

A circuit board of a solid-state image sensor (CCD) in an electronic endoscope apparatus for inspecting internal cavities of the body by inserting an electronic endoscope having the CCD at one end thereof into an object of inspection and displaying the image of the object on a monitor. The circuit board has a package to which the CCD is attached. A groove portion is provided at one end of the package and connecting terminals are disposed on the upper surface and the under surface of the groove portion. A substrate with a wiring pattern formed both sides thereon is fitted into the groove portion and the circuits are connected. In an endoscope in which the image picked up by the CCD is reversed side by side, the substrate is connected upside down to the package. Thus, this circuit board facilitates correspondence to various structures of endoscopes. Reduction of the diameter of the endoscope is also possible.

4 Claims, 4 Drawing Sheets

(a)

(b)

CIRCUIT BOARD OF SOLID-STATE IMAGE SENSOR FOR ELECTRONIC ENDOSCOPE

This application is a continuation of application Ser. No. 07/866,575 filed Apr. 10, 1992.

BACKGROUND OF THE INVENTION

1. Field of the Invention

The present invention relates to a circuit board of a solid-state image sensor for an electronic endoscope and, more particularly, to the structure of a circuit board to which a solid-state image sensor which is disposed in an electronic endoscope is attached.

2. Description of the Prior Art

An electronic endoscope apparatus is an instrument for inspecting internal cavities of the body by inserting an electronic endoscope, which is a scope, into an object of inspection such as an internal cavity of the body or a vomica and displaying the image of the object of inspection on a monitor. For example, a solid-state image sensor such as a CCD (charged coupled device) is mounted on one end of the electronic endoscope. FIG. 5 shows the structure of the end portion of such an electronic endoscope. As shown in FIG. 5, the end surface of an electronic endoscope 1 is provided with an observation window 2 for observing the object of inspection and picking up the image of the object therethrough, and a forceps insertion hole 3. A manipulating tool insertion channel 4 is provided so as to communicate with the forceps insertion hole 3, thereby making it possible to pick a tissue in a cavity of the body with a forceps or the like inserted into the manipulation tool channel 4.

An objective 5 is provided on the inside of the observation window 2, and a CCD 8 held by a package 9 is disposed at the following stage of the objective 5 through a prism 7. The CCD 8 is attached to the under surface of the prism 7 so that light which is refracted by the prism 7 enters the CCD 8. The CCD 8 is attached to the package 9 of a ceramic material by bonding wires, and the package 9 protects the CCD 8 from the influence of the environment such as heat and noise. The package 9 is attached to a substrate 10 composed of a rigid sheet by bonding wires. Signal cables 11 are connected to the substrate 10 and an electronic part is disposed thereon.

According to the above-described structure, the image of the object of inspection which enters the objective 5 through the observation window 2 is supplied to the imaging surface of the CCD 8, and the video signals obtained by the CCD 8 are output to the circuit formed on the substrate 10 and supplied to the processing unit in the main body through the signal cables 11.

Since the above-described conventional circuit board of the solid-state image sensor for an electronic endoscope is integrally connected to the CCD 8 and the package 9 by wire bonding, a circuit board having a suitable connection to an endoscope must be produced in correspondence with each type of endoscope. For example, with respect to the arrangement of the CCD 8, in a horizontal type endoscope, the CCD 8 is disposed in parallel to the axis of the endoscope (the direction in which light enters), as shown in FIG. 5, while in a vertical type endoscope, the CCD 8 is disposed vertically to the axis of the endoscope (the direction in which light enters). With respect to the position of the observation window, in a direct looking type endoscope, the observation window 2 is disposed at the front of the endoscope (in the axial direction), as shown in FIG. 5, while in a side looking type endoscope, the observation window 2 is disposed on the side surface of the endoscope 1 so as to observe the object of inspection from the side surface. In all of the above-described types, when the prism 7 is used, since light is reflected by the prism 7, the image is reversed side to side, and the connection between the CCD 8 and the substrate 10 must therefore be reverse to that in the case of not using the prism 7. Therefore, a circuit board which is produced for a certain type of endoscope cannot be used as a circuit board for another type of endoscope. In addition, in order to accommodate predetermined circuit parts within a narrow end portion of an electronic endoscope, the shape and the like of the substrate 10 must be changed. In such a case, the circuit board must be completely renewed.

An electronic endoscope is required to reduce the diameter of the end portion as much as possible. In the above-described structure shown in FIG. 5, it is impossible to meet such demand sufficiently.

SUMMARY OF THE INVENTION

Accordingly, it is an object of the present invention to eliminate the above-described problems in the prior art and to provide a circuit board of a solid-state image sensor for an electronic endoscope which is capable of corresponding to various types of electronic endoscopes, which facilitates a change in the specification, and which is capable of reducing the diameter of the endoscope.

To achieve this end, the present invention provides a circuit board having a package to which a solid-state image sensor provided at the end portion of an electronic endoscope is attached, the circuit board comprising: a substrate with a wiring pattern formed on both sides thereof; a package with a groove portion formed at one end thereof such that the substrate is fitted thereinto; and connecting terminals disposed on the upper surface and the under surface of the groove portion so as to connect the substrate and the package.

According to the above-described structure, the substrate with the wiring pattern formed on both sides thereof is fitted into the groove portion of the package so as to connect the substrate and the package. If, for example, the terminals for connecting the package and the substrate are through-hole terminals, the package and the substrate are securely connected to each other by pouring a solder into the through-hole terminals. This method makes it easy to connect the substrate upside down to the package, thereby enabling the connection of various types of substrates to one type of solid-state image sensor. Thus, it is possible to produce a circuit board which is fit for endoscopes of various types.

The above and other objects, features and advantages of the present invention will become clear from the following description of the preferred embodiments thereof, taken in conjunction with the accompanying drawings.

BRIEF DESCRIPTION OF THE DRAWINGS

FIGS. 1(a) and 1(b) show the structure of an embodiment of a circuit board of a solid-state image sensor for an electronic endoscope according to the present invention, wherein FIG. 1(a) is a perspective view of the circuit board and FIG. 1(b) is a partially sectional view of the circuit board incorporated into a horizontal type electronic endoscope;

DESCRIPTION OF THE PREFERRED EMBODIMENTS

Figure 1:
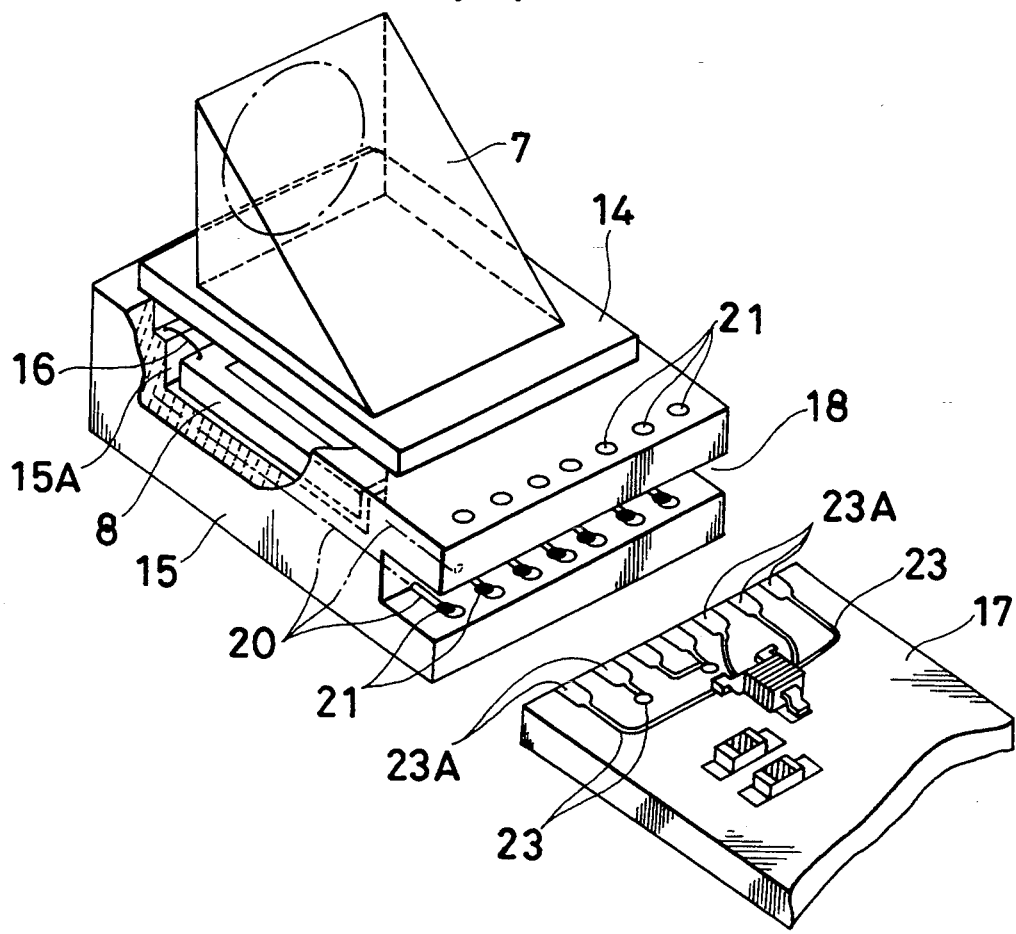
Figure 1:
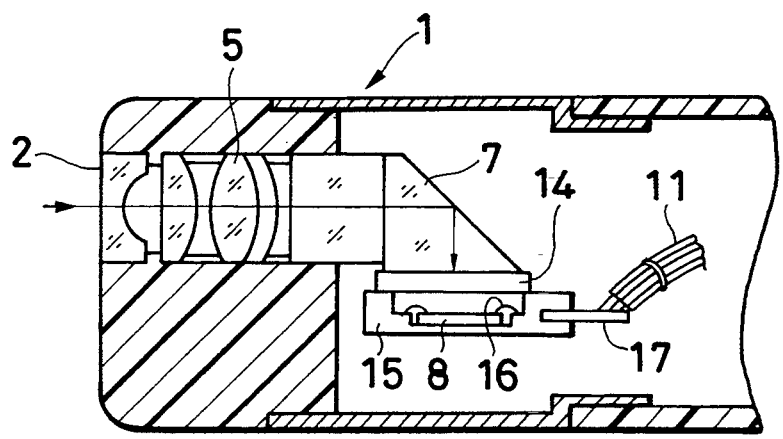
Figure 2:
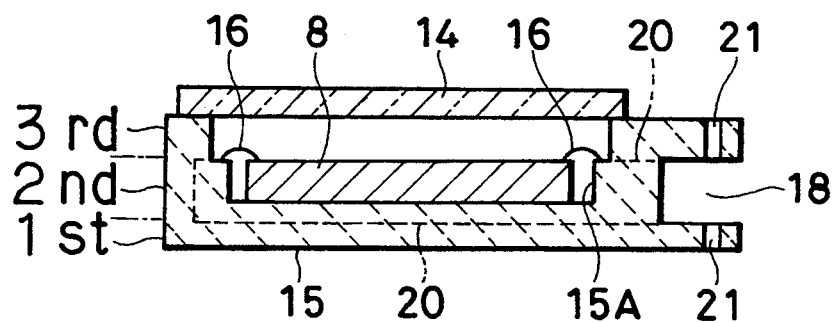
FIG. 2 is a sectional view of the package shown in FIGS. 1(a) and 1(b)

FIG. 1 shows the structure of an embodiment of a circuit board of a solid-state image sensor for an electronic endoscope according to the present invention. As shown in FIG. 1, a package 15 which is connected to a CCD 8 is attached to a prism 7 through a cover glass 14. The package 15 is composed of a ceramic box and connected to the CCD 8 accommodated in a square recessed portion 15A by bonding wires 16. A groove portion 18 for fitting a circuit board 17 thereinto is provided at one end of the package 15. As shown in the sectional view of the package 15 in FIG. 2, the package 15 is composed of three layers of ceramic sheets. The recessed portion 15A for accommodating the CCD 8 is formed on the second layer, and the groove portion 18 having a space which corresponds to the thickness of the substrate 17 is formed at the right end portion in FIG. 2. Wiring patterns 20 for connecting the CCD to the package 15 are formed ranging from the CCD connecting portion to the upper surface and the under surface of the groove portion 18, as shown in FIG. 2. Through-hole terminals 21 and lands (not shown) are formed on the upper surface and the under surface of the groove portion 18 so as to be connected to the wiring patterns 20.

The substrate 17 shown in FIG. 1 is fitted into the groove portion 18 of the package 15. An electronic part 22 is attached to the substrate 17, and wiring patterns 23 including lands 23A are formed on the top and bottom surfaces of the substrate 17.

Figure 3:
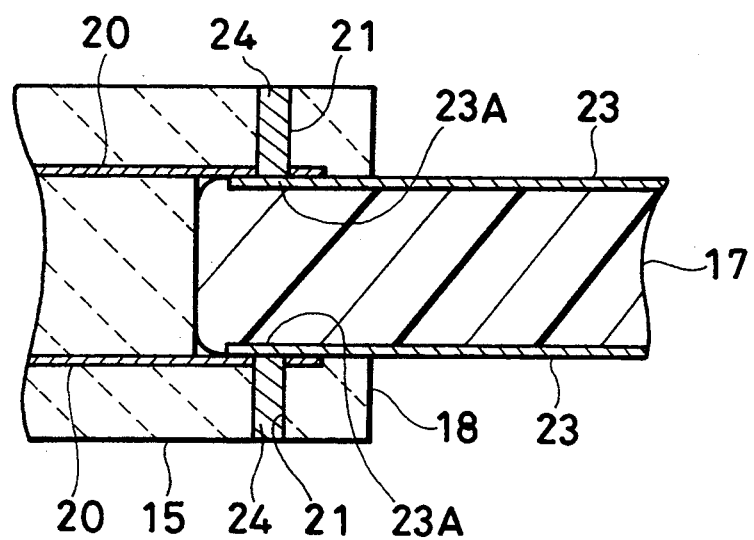
FIG. 3 is a sectional view of the substrate connected to the groove portion of the package.

FIG. 3 shows the package 15 connected to the substrate 17. As shown in FIG. 3, after the substrate 17 is fitted into the groove portion 18 of the package 15, a viscous solder or conductive adhesive 24 is poured into and fill in the through-hole terminals. In this manner, the through-hole terminal s 21 and the lands 23A of the substrate 17 are electrically connected and also mechanically firmly fixed. The substrate 17 and the groove portion 18 may be connected by pins or the like driven into the through-hole terminals 21 in place of using a solder or the like.

FIG. 1(b) shows the final state in which the circuit board of a solid-state image sensor of this embodiment is attached to an electronic endoscope. The electronic endoscope is a horizontal type or a direct looking type. In this case, since a prism 7 is used, the image picked up by the CCD 8 is reversed side to side. The substrate 17 is therefore connected in such a manner as to correct the mirror image (connected upside down). In the case of a side looking type endoscope which does not use the prism 7 and which is provided with an observation window on the side surface thereof, the upper surface and the under surface of the substrate 17 are reversed to those shown in FIG. 1(b). Compared with the conventional circuit board shown in FIG. 5, since the substrate 17 in this embodiment is accommodated in the package 15, the thickness of the substrate 17 (corresponding to the thickness of the substrate 10) is included in the thickness of the package ]5. In other words, in this embodiment, it is possible to reduce the diameter of the endoscope by the thickness of the substrate (10) as compared with the prior art. According to this structure, it is possible to handle the package 15 for holding the CCD 8 and the substrate 17 separately from each other, and to attach another type of substrate to the package 15. For example, it is easy to attach an L-shaped substrate which will be described in the following with reference to FIG. 4 to the package.

Figure 4:
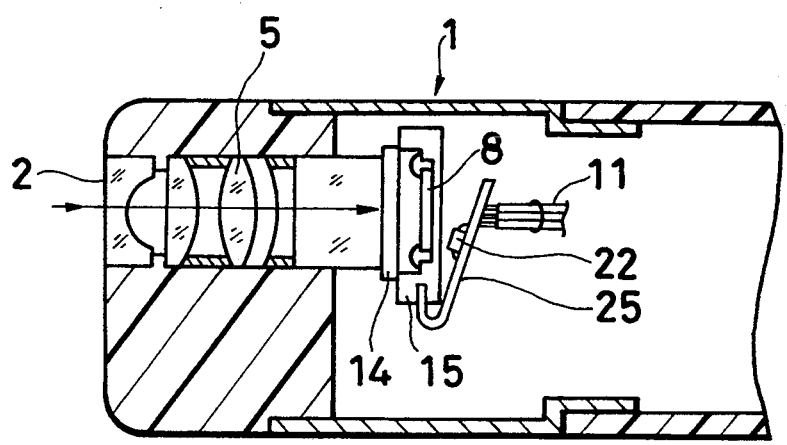
FIG. 4 is a partially sectional view of the circuit board incorporated into an elevation type electronic endoscope.
Figure 5:
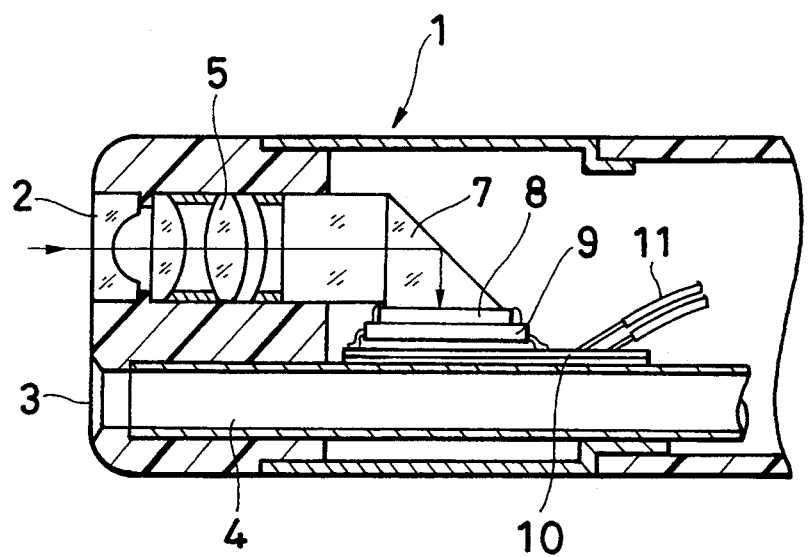
FIG. 5 is a partially sectional view of the structure of the end portion of a conventional electronic endoscope.

FIG. 4 shows another embodiment of a circuit board of a solid-state image sensor applied to a direct looking and elevation type electronic endoscope. As shown in FIG. 4, in this case, no prism is used and the package 15 having the CCD 8 is attached to an optical system having an objective 5 through the cover glass 14. An L-shaped substrate 25 is fitted into the groove portion 18 so as to electrically connect the L-shaped substrate 25 and the groove portion 18. Signal cables 11 are connected to the back side of the L-shaped substrate 25. In this case, since no prism is used and the image is not reversed side to side, the substrate 25 is not turned upside down for connection. In other words, in the state in which the L-shaped substrate 25 is connected to the package 15, the top surface and the bottom surface are reverse to those of the substrate 17 shown in FIG. 1(b). In a side-looking elevation type endoscope which uses a prism, the top surface and the under surface of the L-shaped substrate 25 are reversed to those shown in FIG. 4.

As described above, according to the present invention, since it is possible to use the package 15 separately from the substrate 17 (25), it is easy to produce any given circuit board in correspondence with the structure of an electronic endoscope of horizontal type, elevation type, direct looking type, side looking type or the like. A change in the specification is also easy. In addition, since the substrate is connected to the groove portion of the package, the diameter of the endoscope is reduced by the thickness of the substrate as compared with the prior art.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A circuit board of a solid-state image sensor for an electronic endoscope comprising:

a package for attaching thereto the solid-state image sensor disposed at one end portion of the electronic endoscope, said sensor having input/output terminals at both ends;

a groove portion formed at one end of the package;

connecting terminals disposed on the upper surface and the under surface of the groove portion of the package portion and connected to the solid-state image sensor; and a substrate which is provided with a wiring pattern on both sides thereof and which is fitted into the groove portion of the package so as to connect the package and the substrate by the connecting terminals, wherein the substrate may be connected with either side facing the upper surface of said groove portion of the package such as to provide an image or a mirror image of video signals picked up by the solid-state image sensor.

2. A circuit board of a solid-state image sensor for an electronic endoscope according to claim 1, wherein a through hole is provided in each of the connecting terminals of the package, and a solder or a conductive adhesive is filled in the through hole so as to connect the package to the substrate.

3. A circuit board of a solid-state image sensor for an electronic endoscope according to claim 1, wherein the solid-state image pickup sensor is disposed horizontally to the electronic endoscope.

4. A circuit board of a solid-state image sensor for an electronic endoscope according to claim 1, wherein the solid-state image pickup sensor is disposed vertically to the electronic endoscope.

* * * * *